(12) United States Patent
Shelton et al.

(10) Patent No.: US 7,934,434 B2
(45) Date of Patent: May 3, 2011

(54) APPARATUS AND METHOD FOR ANALYSIS OF DRY POWDER INHALER PRODUCTS

(75) Inventors: Christopher M. Shelton, Verona, WI (US); Timothy J. Stephens, Watertown, WI (US)

(73) Assignee: Pharmaceutical Product Development, Inc., Rockville, MD (US)

( * ) Notice: Subject to any disclaimer, the term of this patent is extended or adjusted under 35 U.S.C. 154(b) by 647 days.

(21) Appl. No.: 11/948,249

(22) Filed: Nov. 30, 2007

(65) Prior Publication Data
US 2009/0139352 A1    Jun. 4, 2009

(51) Int. Cl.
G01N 1/24 (2006.01)
G01N 1/14 (2006.01)
G01N 1/40 (2006.01)

(52) U.S. Cl. .................. 73/863.23; 73/864.34

(58) Field of Classification Search .......... 15/383; 73/863.23–863.25, 864.34–864.35, 863.86, 73/865.5
See application file for complete search history.

(56) References Cited

U.S. PATENT DOCUMENTS 5,232,808 A * 8/1993 Bonser et al. ............ 430/108.11
2005/0025755 A1 * 2/2005 Hedrick et al. ............ 424/93.21

FOREIGN PATENT DOCUMENTS
JP          60249676 A   * 12/1985

OTHER PUBLICATIONS

"FORADIL® AEROLIZER®" Medication Guide, Copyright 2006, Novartis Parmaceuticals Corporation, 8 pages.
"How to Use The FORADIL AEROLIZER", available at http://www.foradil.us/, printed Nov. 8, 2007, pp. 1-2.
Blanchard et al., "Best Practices for Managing Quality and Safety of Foreign Particles in Orally Inhaled and Nasal Drug Products, and an Evaluation of Clinical Relevance", Pharm. Res. 24(3), 2007, pp. 471-479.
Blanchard et al., "Foreign Particles Testing in Orally Inhaled and Nasal Drug Products", Pharmaceutical Research, vol. 21, No. 12, Dec. 2004, pp. 2137-2147.
Castaldo "Identification of Foreign Particles Below 10 Microns Key to Inhaled Drug Quality", Pharmaceutical Processing, available at http://www.pharmpro.com/, printed Aug. 9, 2007, pp. 1-3.
D'Abreu-Hayling "Quality by Design and Risk Management Approaches to Foreign Particles in OINDP", Respiratory Drug Delivery 2006, pp. 640-642.

(Continued)

*Primary Examiner* — Thomas P Noland
(74) *Attorney, Agent, or Firm* — Sheridan Ross, P.C.

(57) ABSTRACT

An apparatus and method are provided for collection and analysis of dry powder inhaler products to determine foreign particulate matter found therein. The apparatus includes a collection chamber that communicates directly with the mouthpiece of a dry powder inhaler device. The collection chamber is used to both collect product samples, as well as to mix the samples with a diluent that places the active pharmaceutical components and excipients in solution, while the foreign particulate matter remains suspended. Analysis of a sample is preferably conducted by light obscuration wherein a probe is inserted directly within the collection chamber of the apparatus. An integral magnetic stir-bar incorporated within the apparatus eliminates the need to transfer the collected sample to a secondary vessel for mixing or analysis.

6 Claims, 6 Drawing Sheets

OTHER PUBLICATIONS

Hart "Proposal for Foreign Particles Testing in orally Inhaled and Nasal Drug Products", Respiratory Drug Delivery IX, 2004, pp. 521-524.

Kreher et al., "Foreign Particle Characterization in Inhalation Drug Products: A Critical Comparison of Methods and Techniques", Respiratory Drug Delivery IX, Palm Springs, CA, 2004, pp. 373-376.

Neiman et al., "A Critical Comparison: Particle Counting With Light Obscuration and Automated Raman Microscopy", Respiratory Drug Delivery 2006, pp. 529-532.

Neiman et al., "Development of an Integrated Measurement System for Foreign Particles Testing in OINDP Based on IPAC-RS Recommendations", RDD Europe 2005, pp. 181-184.

Pilewski et al., "Determination of Foreign Particulate Matter in Metered Dose Inhalers by Light Obscuration", Respiratory Drug Delivery IX, Palm Springs, CA, 2004, available at www.rddonline.org.

Valet et al., "Method for Foreign Particles Counting and Identification in a Cellulose Containing Suspension of a Nasal Spray", Respiratory Drug Delivery Europe 2007, pp. 325-328.

Valet et al., "Qualification of the Particle Explorer System for Foreign Particles Counting and Identification in a Dry Powder Inhaler Product Based on IPAC-RS Recommendations", Respiratory Drug Delivery 2006, pp. 761-764.

Vicens et al., "System for Measuring the Performance of Microscopic Particle Analyzers", Respiratory Drug Delivery 2006, pp. 433-435.

* cited by examiner

APPARATUS AND METHOD FOR ANALYSIS OF DRY POWDER INHALER PRODUCTS

FIELD OF THE INVENTION

The present invention relates to an apparatus and method for analyzing dry powder drugs administered by an inhaler device, and more particularly, to an apparatus and method directed to the collection and enumeration of foreign particulate matter found in an emitted dose from a dry powder inhaler device.

BACKGROUND OF THE INVENTION

The analysis of foreign particulate matter in orally inhaled and nasal drug products (OINDPs) is an area of recent concern within the pharmaceutical industry. Through various research efforts to include work conducted by the Environmental Protection Agency in development of its air quality standards, particulate matter of very small size has been shown to have the capability to penetrate the deepest parts of the lungs. The EPA has concluded that a link exists between fine particulate matter and numerous health problems including asthma, bronchitis, and various other acute and chronic respiratory symptoms. The pharmaceutical industry has taken it upon itself to conduct various studies to determine the extent to which to foreign particulate matter may have contaminated OINDP products by developing methods of obtaining samples of such products in order to identify and quantify the particulate matter. Foreign particulate matter may originate from a number of sources to include, for example, drug-manufacturing processes, particles found in the inhaler devices that are used to deliver the drug product and others.

Accordingly, a number of techniques are currently used to analyze and enumerate foreign particulate matter in OINDPs. Such techniques may include optical microscopy, SCM/EDX, light obscuration, electrical resistance, and use of a Raman probe. Microscopic techniques offer some advantages in that samples taken allow for collection of both qualitative and quantitative data, i.e., composition and enumeration of the particulate matter found. While obtaining the composition and enumeration of the particulate matter is essential to understanding the potential sources of particulate contamination during product development, such microscopic techniques are laborious and are simply not efficient for routine monitoring of particulate matter. Furthermore, microscopic techniques are inherently subjective and substantial variances in collected data can result. Particulate matter analysis of dry powder inhaler products using microscopy is typically performed by microscopic analysis of insoluble particles collected on a substrate following a filtration of a solution containing the dry powder drug formulation.

Light obscuration techniques generally allow for faster analysis times and larger sample sizes, while removing analysis subjectivity. Additionally, the larger quantity of data obtained through light obscuration techniques can be used to generate statistical evaluation of results over time as part of a stability study. While light obscuration techniques may be known for analysis of foreign particulate matter, there is still a need for methods that optimize efficient and accurate collection of samples so that multiple samples can be obtained at minimum cost and effort.

A number of published articles address the analysis of foreign particulate matter found in dry powder drug products delivered to a user, and these articles specify various collection and analysis techniques. One such article is entitled "Determination of Foreign Particulate Matter in Metered Dose Inhalers (pMDI) by Light Obscuration" (Respiratory Drug Delivery IX, 2004, Pilewski, et al). In this article, light obscuration is used as the method of analysis, and collection of the sample is achieved by multiple actuations of an inhaler device that expels the drug into a diluent held in a trace clean jar. The samples are then filtered and analyzed by light obscuration. The article entitled: "Proposal for Foreign Particles Testing in Orally Inhaled and Nasal Drug Products" (Respiratory Drug Delivery IX, 2004, Hart) discloses various techniques for the analysis of foreign particles to include a comparison of the capabilities and limitations of the various techniques. The article entitled: "Foreign Particles Testing in Orally Inhaled and Nasal Drug Products" (Pharmaceutical Research, Vol. 21, No. 12, December, 2004) provides a summary of industry best practices for testing and controlling foreign particles in OINDPs and provides proposals for developmental characterization and quality control strategies for foreign particles.

While efforts have been made to characterize foreign particulates and to develop various methodologies for sampling and analyzing drugs that have foreign particulate matter, there is still a need for a sampling method and analysis method that allows for faster analysis times, larger sample sizes, while removing as much operator subjectivity as possible without compromising industry accepted standards for conducting such sampling and analysis methods. There is also a need for provision of collection and mixing apparatuses that simplify the methods of sampling and analysis to particularly limit foreign particulate matter from entering a sample that did not originate from the drug as it was packaged and delivered by the recommended inhaler device.

SUMMARY OF THE INVENTION

In accordance with the present invention, an apparatus and method are provided for analysis of dry powder inhaler products. In one aspect of the invention, a particulate matter collection apparatus is provided that is used to collect a dry powder drug sample and to hold a solution containing the dissolved drug wherein suspended foreign particulate matter in the solution is analyzed. The particulate matter collection apparatus is connected directly to an inhaler device that is normally used to deliver emitted doses of the drug.

In another aspect of the invention, it includes the combination of a particulate matter collection apparatus and an inhaler device wherein the dry powder inhaler product is transferred to a collection chamber within the collection apparatus by assistance from a vacuum drawn through the collection chamber.

In yet another aspect of the present invention, a method is provided for collecting and enumerating foreign particulate matter as an emitted dose from dry power inhaler products.

In yet another aspect of the invention, a method is provided for collecting a sample from the dry powder inhaler products wherein subsequent analysis by light obscuration can be conducted or in combination with other testing or analysis protocols.

The collection apparatus serves a two-fold purpose, the first being a receptacle for receiving a delivered dose of the dry powder inhaler product, and the second being a mixing vessel for receiving a quantity of solution. The solution is used to dissolve the dry powder inhaler product and to suspend foreign particulate matter thereby enabling subsequent analysis by light obscuration. The collection apparatus includes an integral mixing assembly that allows mixing to take place directly within the collection chamber of the collection apparatus thereby eliminating the need to transport the sample that otherwise could inadvertently introduce further particulate matter to the sample. Preferably, the mixing assembly includes a magnetic stir-bar that is suspended within the collection chamber. Mixing the solution added to the collection chamber is achieved by placing the collection apparatus on a magnetic stir-plate, which thereby activates movement of the magnetic stir-bar.

One end of the collection apparatus is adapted to connect to the dry powder inhaler device. The opposite end of the collection apparatus is adapted to connect to a source of vacuum, which allows the dry powder product to be drawn through the inhaler device and into the collection chamber when the vacuum device is activated. When the vacuum is pulled, a filter disposed in the collection chamber captures the inhaler product, as well as any foreign particulate matter. The filter is preferably a robust sintered metal filter that can withstand the vacuum force as well as forces transferred to it during mixing In accordance with the methods of the present invention, once the inhaler product and foreign particulate matter is captured on the filter, the vacuum source is disconnected and the inhaler device is also disconnected from the collection apparatus. Conveniently, the collection apparatus includes bayonet-style fittings at opposite ends of the apparatus that allows caps to be placed on both ends of the collection apparatus thereby sealing the captured inhaler product and foreign particulate matter within the collection chamber. A solution is added to the collection chamber through the open-end of the collection apparatus previously connected to the inhaler device. An upper cap then seals that end of the collection apparatus. The solution is mixed within the collection chamber to dissolve the dry powder product and to suspend the foreign particulate matter. A series of mixing steps may be performed to include mixing by use of the integral magnetic stir-bar, mechanical mixing by inversion of the collection apparatus, as well as sonification. Once adequate mixing is completed, sampling of the chamber contents can take place. In accordance with the preferred embodiment of the present invention, the method of analysis is by light obscuration. The upper cap of the collection chamber is removed and a sampling probe of a particle-counting device is inserted within the solution. Particle counts are obtained in one or more samples drawn from the solution.

There are numerous advantages to the present invention. The collection apparatus serves the dual purpose of providing a receptacle for a delivered dose of the dry powder product, as well as serving as the mixing vessel that allows direct sampling and particulate analysis by light obscuration. A robust filter is provided that allows for adequate air-flow to facilitate collection of the emitted dry powder inhaler product, yet the filter is able to withstand the rigorous mixing steps required to dissolve the active and excipient ingredients of the dry powder inhaler formulations. The integral magnetic stir-bar incorporated within the structure of the collection apparatus eliminates the need to transfer the collected sample to a secondary vessel for analysis. Structurally, the collection apparatus provides for an efficient and reliable means to receive a delivered dose and to mix the delivered dose with a selected solution.

Other features and advantages of the present invention will become apparent from a review of the following detailed description, taken in conjunction with the drawings.

DETAILED DESCRIPTION

Figure 1:
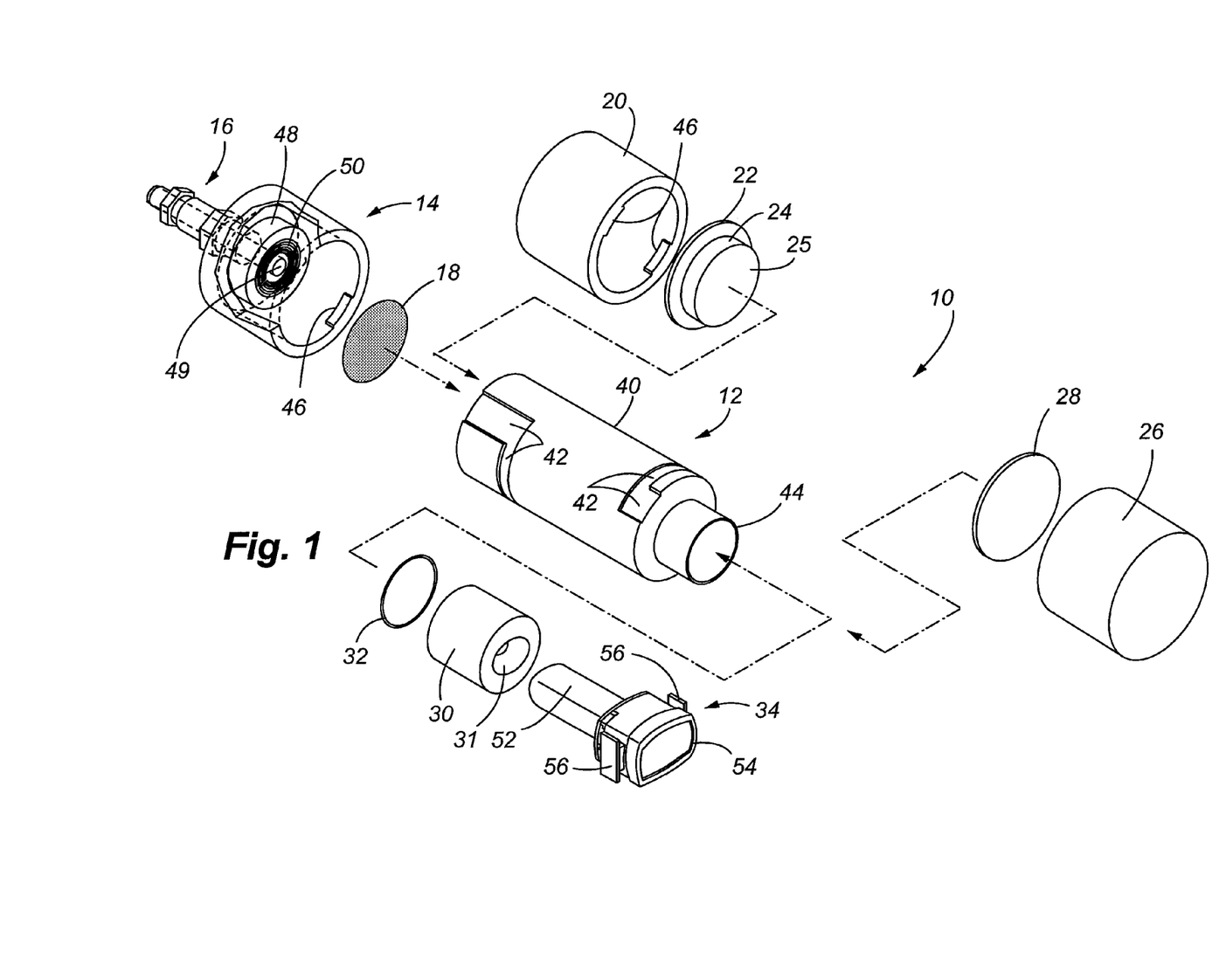
FIG. 1 is an exploded perspective view of the particulate matter collection apparatus of the present invention and a dry powder inhaler device used to deliver a dose of the drug to be analyzed for foreign particulate matter.
Figure 2:
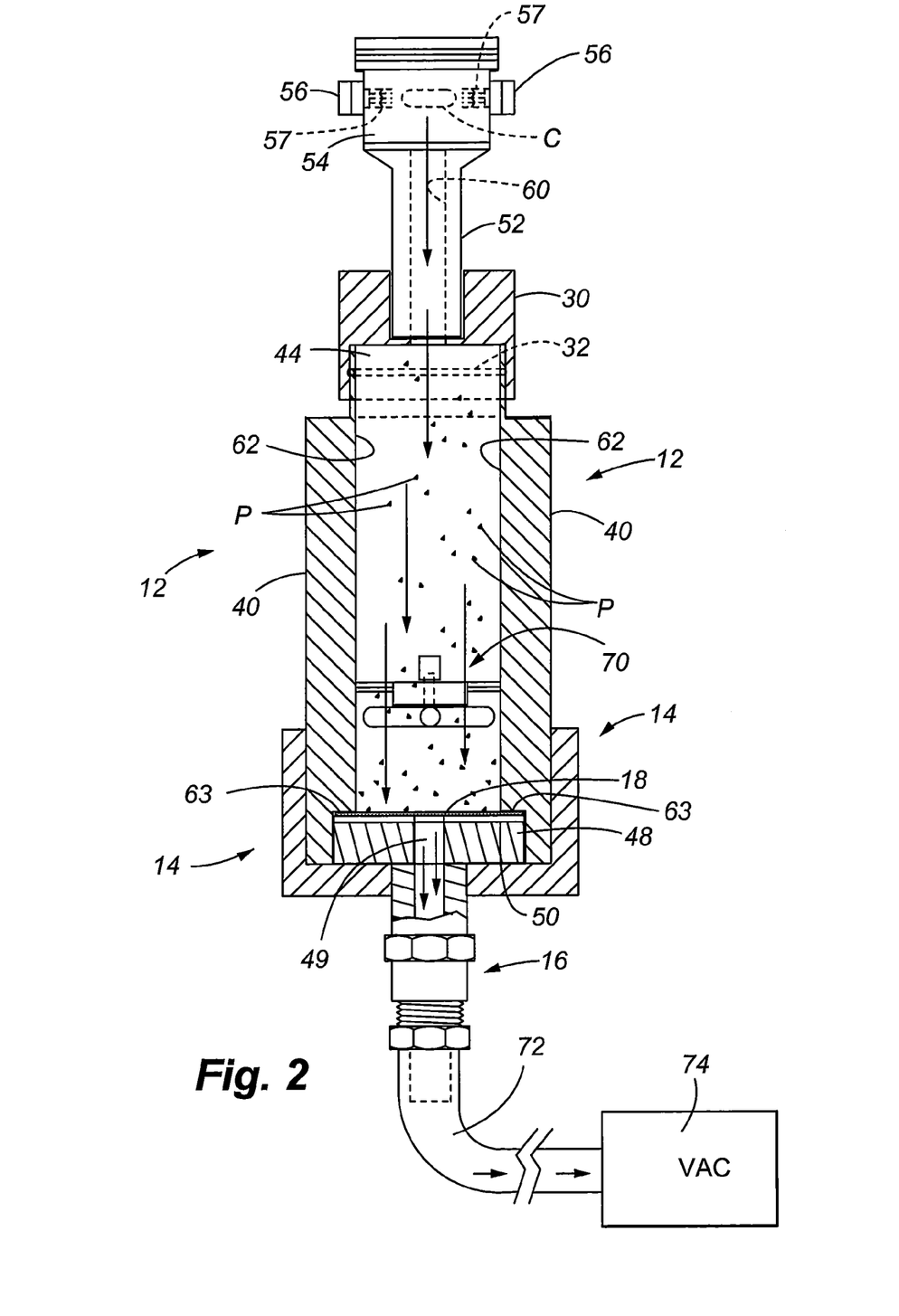
FIG. 2 is an enlarged cross-sectional view of the collection apparatus connected between a source of vacuum and the dry powder inhaler device.

Referring to FIG. 1, the particulate matter collection apparatus 10 of the present invention is illustrated along with an example of an inhaler device 34. Referring first to the structure of the collection apparatus, it includes a body 12 that defines an internal collection chamber. As shown, the body 12 is cylindrical shaped, and a flange 44 extends beyond one end of the body. Referring also to FIG. 2, a vacuum adapter 14 is secured to the other end of the body 12 for purposes of pulling a vacuum through the collection apparatus as discussed further below. The vacuum adapter 14 includes a vacuum fitting 16 that is secured to the closed end of the vacuum adapter 14. The vacuum fitting 16 communicates with an orifice 49 that is formed through the vacuum adapter. A raised filter seat 48 protrudes into the vacuum adapter and the orifice 49 is centrally formed through the raised filter seat 48. A pattern of concentric grooves 50 is formed on the exposed surface of the raised filter seat 48. A collection filter 18 is placed on the raised filter seat and is centered over the concentric grooves 50. When a vacuum is pulled through the collection apparatus, the concentric grooves distribute the vacuum such that a vacuum is experienced over substantially all or most of the collection filter 18. With respect to materials, the collection apparatus may be made of a Delrin® polymer material. The filter may be a sintered metal filter, such as a Porvair® 1875-10-00003C, 47 millimeter, 1 micron absolute in gas/steam. The body 12 has bayonet grooves 42 formed on the outer surface 40 in order that the body may connect to the various components of the collection apparatus. With respect to the vacuum adapter 14, it includes a pair of opposing locking tabs 46 that mate with the bayonet grooves 42 thus completing a standard bayonet connection between the vacuum adapter 14 and the body 12.

As also discussed below, once the dry powder product has been drawn into the collection chamber, the vacuum adapter 14 is replaced with a lower or base end cap 20. End cap 20 also includes a pair of locking tabs 46 for connecting the end cap 20 to the body 12. A gasket 22 is seated within the end cap 20, and a spacer 24 extends from the gasket 22. The filter 18 resides on the upper exposed surface 25 of the spacer 24 once the end cap is secured.

The inhaler device 34 shown in FIG. 1 represents a common commercial inhaler device. Therefore, it shall be understood that the present invention is not limited to use of the collection apparatus with any particular inhaler device. The specific inhaler device illustrated in FIG. 1 corresponds to the Foradil® Aerolizer®. This dry power inhaler device delivers a dose of a dry powder drug product by the user manually activating the device and then inhaling the product. Referring also to FIG. 2, the inhaler device 34 includes a mouthpiece 52 that connects to a base or body 54. The body 54 has an internal chamber (not shown) that is adapted to receive a capsule housing the dry powder product therein. A pair of spring loaded activation buttons 56 are used to activate the inhaler device to release the dry powder product from the capsule C. More specifically, the user presses both of the activation buttons toward the base 54. The activation buttons 56 are connected to puncturing elements 57 that contact the capsule C thus breaking the capsule C. The user places his/her mouth over the open end of the mouthpiece 52 and then inhales. Air flows into the device through openings (not shown) formed on the base 54 adjacent the buttons 56. This airflow causes the capsule C to spin axially within the internal chamber. The axial spinning movement causes the powder to be extracted from the capsule by centrifugal force. Normally, when the user inhales, the dry powder product is transported from the internal chamber through the mouthpiece 52 into the user's body. In the present invention, to simulate the user inhaling, a vacuum is drawn by a vacuum device 74 through tube 72 that communicates with vacuum fitting 16.

In order to attach the inhaler device 34 to the body 12, a mouthpiece adapter 30 is provided which frictionally engages the flange 44. A gasket 32 resides within the interior of the mouthpiece adapter 30 in order that a good seal is maintained between the flange 44 and the mouthpiece adapter 30. The mouthpiece adapter has a mouthpiece opening 31 that conforms to the shape of the mouthpiece 52 of the inhaler device such that the dry powder product does not inadvertently exit the mouthpiece into the environment but, rather, is only drawn into the collection chamber of the body 12. In order to adapt the present invention to other types of inhaler devices, the particular shape of the mouthpiece adapter 30 can be changed to include a mouthpiece opening 31 that conforms to the shape of the mouthpiece of the particular inhaler device.

FIG. 1 also shows the upper or top end cap 26 which replaces the inhaler device 34 and mouthpiece adapter 30 after the dose of dry powder product has been delivered into the collection chamber, as also discussed further below. This upper or top end cap 26 has a corresponding gasket 28 to ensure a fluid tight seal is formed between the upper end cap 26 and the flange 44. The end cap 26 also has locking tabs 46 (not shown) enabling the end cap 26 to be secured to the body 12 as by a standard bayonet connection.

Figure 3:
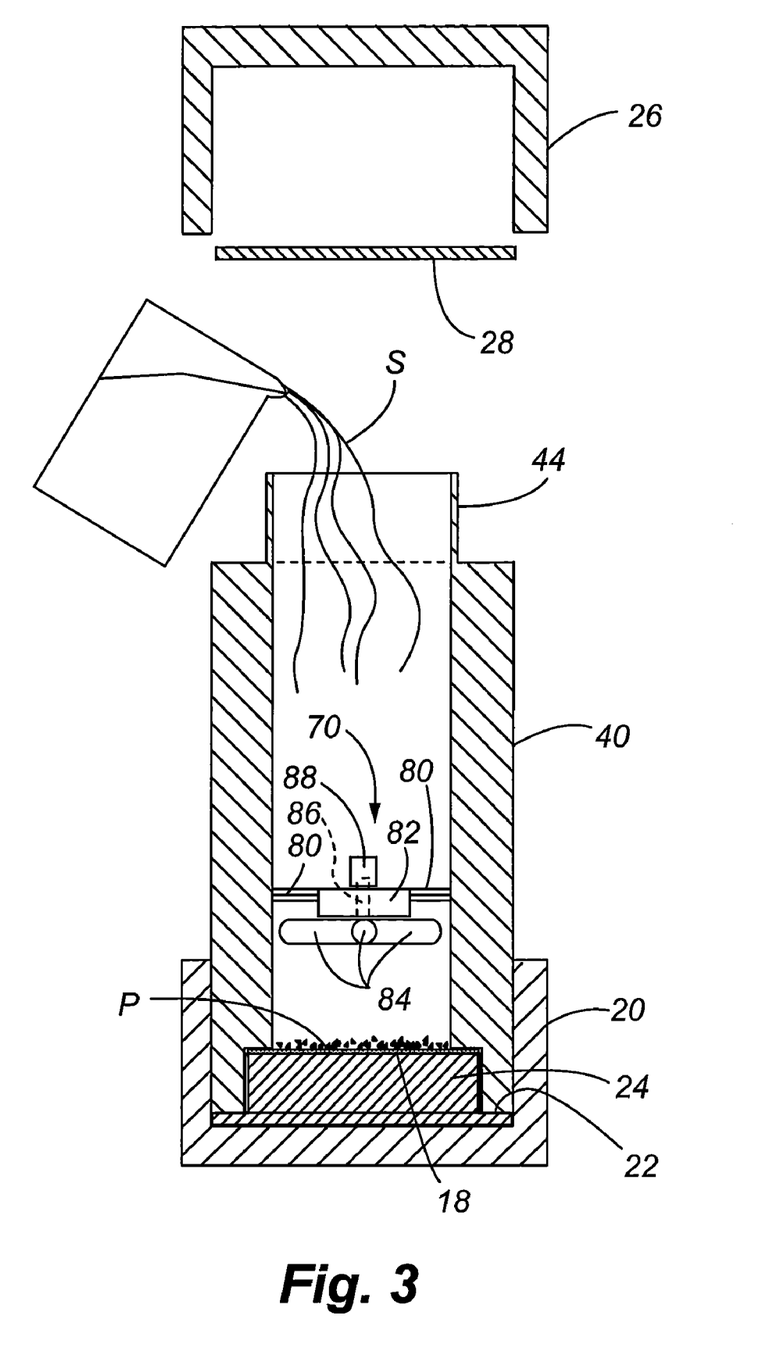
FIG. 3 is a cross section illustrating the collection apparatus disconnected from the vacuum source and sealed at one end of the apparatus while the other end of the apparatus is open to receive a quantity of solution for dissolving the dry powder inhaler product captured by the filter within the collection apparatus.
Figure 7:
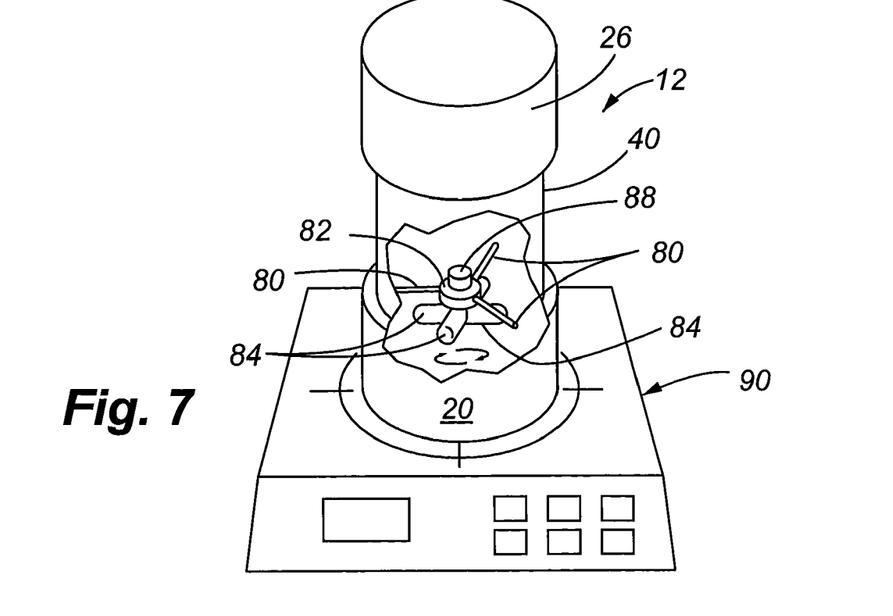
FIG. 7 is a fragmentary perspective view of the collection apparatus with the magnetic stir-bar assembly exposed, and the collection apparatus placed on a conventional magnetic stir-plate for yet further mixing of the solution.

Referring specifically to FIG. 2, the vacuum adapter 14 is shown connected to the body 12, as well as the mouthpiece adapter 30 secured to the body 12 and the inhaler device 34 secured to the mouthpiece adapter 30. The collection chamber of the collection apparatus is defined by the internal wall or interior surface 62 of the body. The collection chamber is cylindrical shaped however the particular shape and size of the collection chamber can be modified to best suit the inhaler device as well as the necessary volume within the collection chamber to accommodate solution added to dissolve the dry powder product. Disposed within the collection chamber is a stir-bar assembly 70 that is used to mix the dry powder product directly within the collection chamber. Referring also to FIGS. 3 and 7, the stir-bar assembly 70 includes a plurality of support bars 80 that extend transversely across the collection chamber and thereby suspend the stir-bar assembly within the collection chamber. The stir-bar supports 80 maybe stainless steel with threaded outer ends that connect to threaded openings formed in the internal wall 62 of the collection chamber. The support bars 80 supports a base 82 that receives a rotatable shaft or pin 86. One end of the shaft or pin 86 is secured by a cap 88 that rests on the base 82. The opposite end of the pin or shaft 86 connects to a stir-bar arrangement, shown as four stir-bar sections 84 formed in a cross pattern. The stir-bar sections are made from a magnetic material and coated with a non-reactive material such as a fluoropolymer coating. When the collection apparatus is immersed in a magnetic field, the stir-bar sections will spin thus mixing the contents within the collection chamber.

Now referring to FIGS. 2-9, the methods of the present invention will be explained. After the necessary suitability tests have been taken with respect to analyzing a blank collection to assess suitability against method specific criteria, a dose of a dry powder inhaler product may be analyzed. The components are assembled as shown in FIG. 2, and a dose of the dry powder inhaler product is delivered by depressing the spring-loaded activation buttons 56. Prior to this activation, the vacuum pump 74 is activated to draw a vacuum through the collection chamber.

As shown in FIG. 2, the dry powder product is drawn through the chamber of the inhaler device, through the passageway within the mouthpiece 52, and into the collection chamber. As the vacuum continues to be drawn, the dry powder product as well as foreign particulate matter collects upon the filter 18.

The method of delivering the emitted dose can be more specifically described as set forth in the U.S. Pharmacopeia §601, "Metered Dose Inhalers and Dry Powder Inhalers, Delivered Dose Apparatus B". Depending upon the particular product, it may be necessary to deliver multiple doses to the collection apparatus so that sufficient resolution of foreign particle matter can be obtained.

Figure 4:
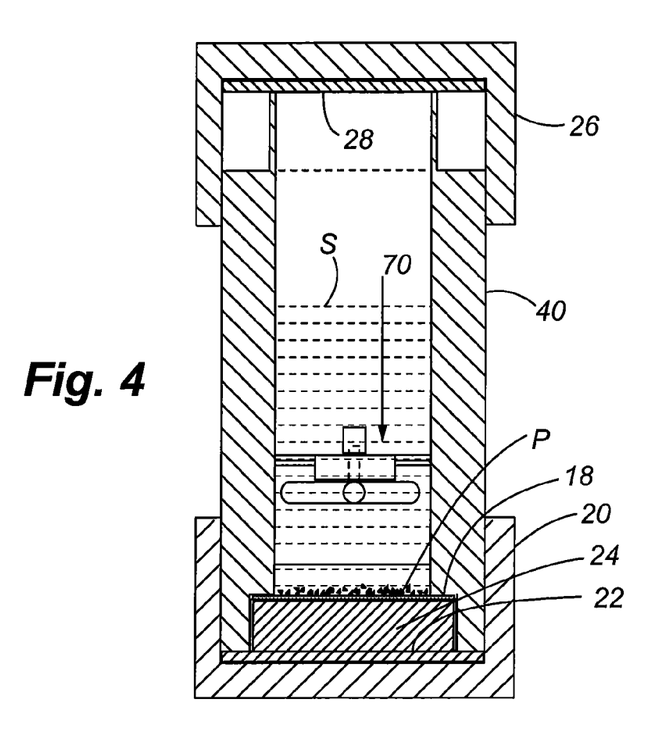
FIG. 4 is another cross-sectional view illustrating the collection apparatus with solution added to the collection chamber and the upper end of the chamber sealed by an upper cap wherein the collection chamber is therefore prepared for mixing.

As shown in FIG. 3, the next step in the process is to shut off the vacuum source, disconnect the vacuum adapter 14, and replace it with the bottom cap 20. To do this, the vacuum fitting 16 can be disconnected from the vacuum line 72, and then the collection apparatus 10 is inverted such that the filter 18 will rest on the circular interior flange 63 of the body 12 when the vacuum adaptor 14 is removed. Then, the vacuum adapter 14 is removed and the cap 20 is connected to the body 12. The gasket 22 seals the connection between the cap and the body. The filter 18 is centered over the exposed surface 25 of the spacer 24. As discussed above, the cap 20 includes locking tabs 46 that are used to create the bayonet connection with the body 12. Once the cap 20 is in place, the collection apparatus 10 may be inverted again and the mouthpiece adapter 30 is separated from the flange 44. A diluent solution S is then added to the collection apparatus. During testing, it was found that a 50 ml aliquot of diluent was sufficient for dissolving the dry powder product and to suspend foreign particulate matter for initial mixing. Once the solution is added, the upper cap 26 is secured over the flange 44, and the locking tabs on the upper end cap 26 are used to make the bayonet connection with the body 12. FIG. 4 shows the solution S added to the collection chamber with the end cap 26 replacing the mouthpiece adapter 30.

Figure 5:
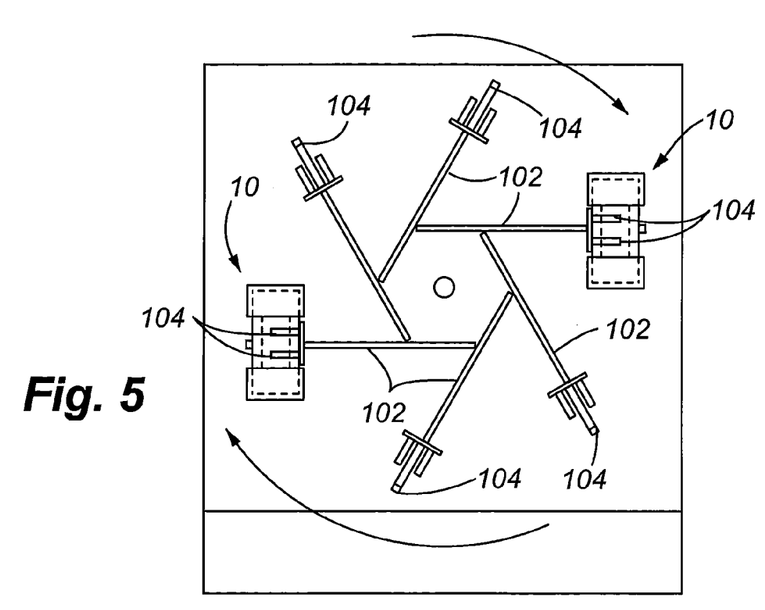
FIG. 5 is a schematic view of a conventional mechanical inversion mixer that can be used to mix the collection apparatus.

Referring to FIG. 5, the collection apparatus is then subject to mixing, such as by mechanical inversion by use of a conventional mechanical mixing apparatus. As shown in FIG. 5, the example mixing device includes rotating arms 102 with grasping tongs 104 that are capable of securing a plurality of collection apparatuses. The collection apparatus is mixed for a predetermined period of time, such as fifteen minutes. The cap 26 is removed, and additional diluent solution is added to the collection apparatus, such as another 50 ml of diluent.

Figure 6:
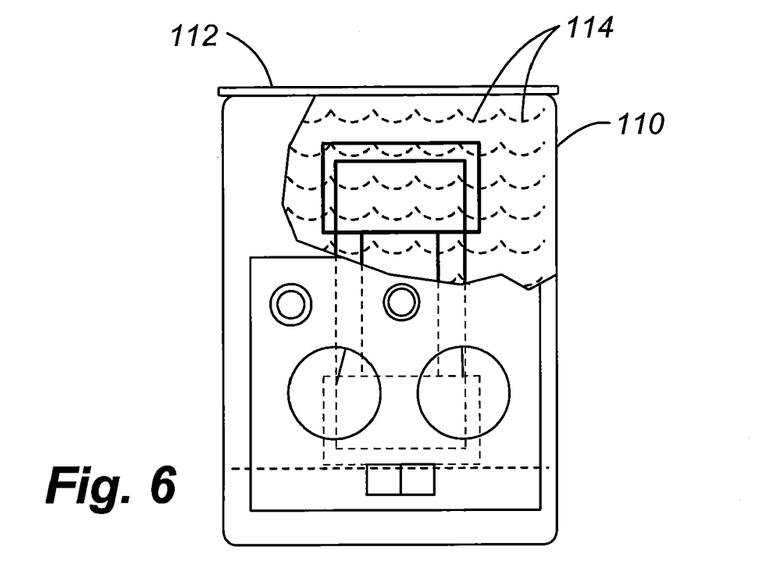
FIG. 6 is a fragmentary elevation view of the collection apparatus placed in a conventional ultrasonic bath to facilitate further mixing.

Referring to FIG. 6, the collection apparatus is then placed within a sonification device to further mix the solution. As shown, the sonification device 110 represents a standard sonification device wherein the collection apparatus 10 is placed within the sonification device through lid 112. A volume of fluid 114 fills the sonification chamber of the sonification device 110 and the collection apparatus is then sonificated for a predetermined amount of time in an ultrasonic bath.

Referring to FIG. 7, the last mixing step is achieved by placing the collection apparatus on a magnetic stir-plate 90. The magnetic stir-place 90 shown in FIG. 7 represents a standard magnetic stir-plate. When the stir-plate is energized, the magnetic field causes the stir sections 84 to rotate, thereby mixing the solution within the collection chamber. One example of a magnetic stir-plate that can be used is a Fisher Scientific Model No. 11-510-49SHQ.

Figure 8:
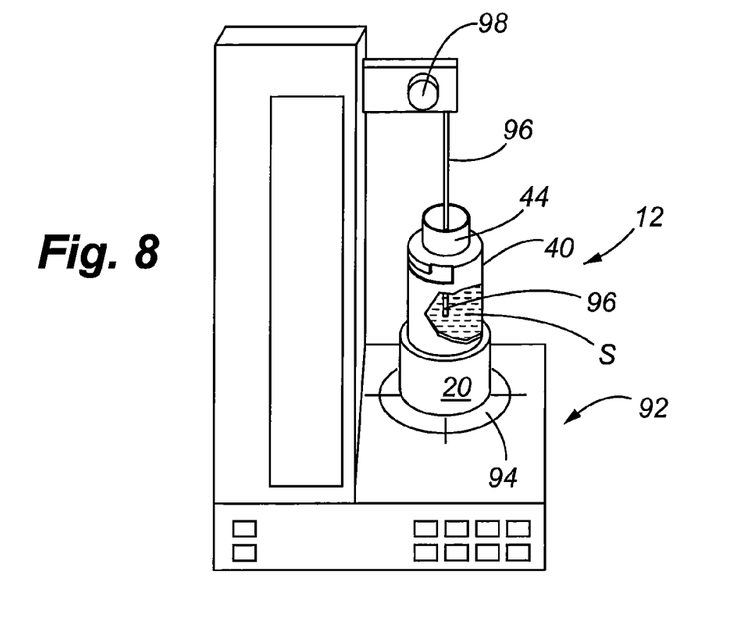
FIG. 8 is a fragmentary perspective view of the collection apparatus during analysis of foreign particulate matter by use of a particle counting device including a sampling probe placed within the collection chamber.

After mixing is completed as by use of the magnetic stir-plate, the sample may now be analyzed. Referring to FIG. 8, the collection apparatus is moved to a particulate counting device 92. The top or upper cap 26 is removed, and the collection apparatus is positioned so that a probe 96 of the device 92 is inserted within the collection chamber. One example of a particle-counting device that may be used includes the HIAC Royko Model 9703 with HRLD 400 sensor. This particle-counting device has the capability of monitoring various channels that can be set by the operator. For example, in the present invention channels that can be monitored may include 2, 5, 10, 25, 50, 100 and 300 microns. The sample analysis drawn can be, for example, in four draws each of 5 ml from the sample. The first draw can be discarded, and the mean average of the second, third and fourth draws can be reported. In connection with the Royko device illustrated, the sensor unit 98 is disposed above the probe 96, and this device also includes an integral stir-plate 94. Therefore, this particular device can be used both for mixing and analysis.

Figure 9:
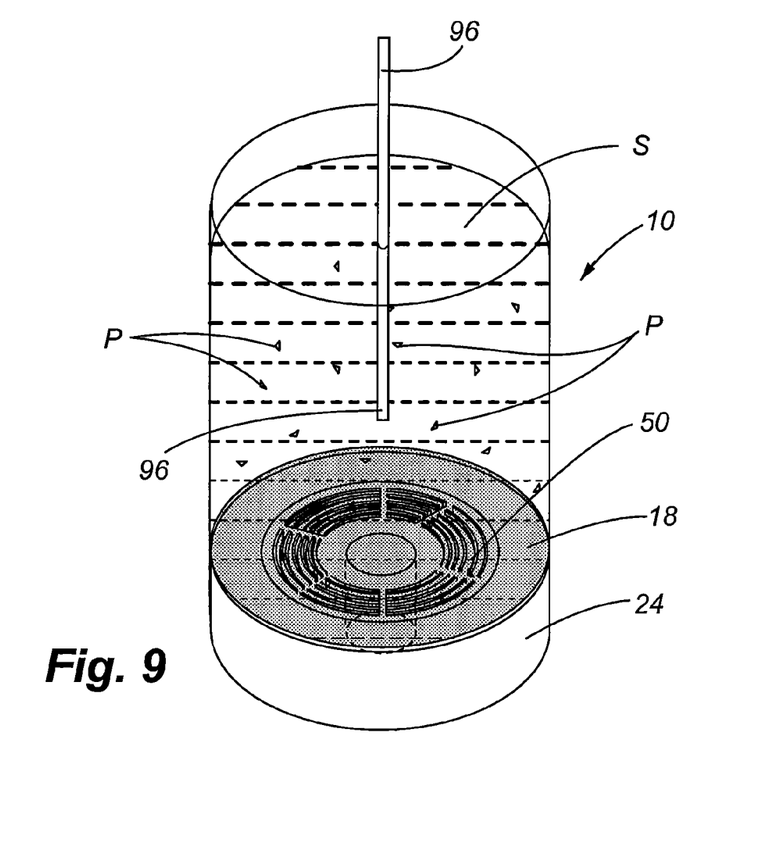
FIG. 9 is a greatly enlarged schematic view of the collection apparatus and the probe of the particle counting device that is used to enumerate the foreign particulate matter.

FIG. 9 is a greatly enlarged schematic of the collection chamber illustrating the probe 96 within the collection chamber wherein active pharmaceutical ingredients and excepients are placed in solution, but the foreign particulates P remain suspended which allows the probe to operate such that the instrument can withdraw the sample aliquot to enumerate particle sizes in the sample by light obscuration.

At any point in time of the processing of the sample, a laminar flow environment can be used to minimize additional foreign particulate matter from entering the collection chamber that would otherwise affect true particle counts. Particularly during sampling of the solution, placement of the particle counter in a laminar flow environment is particularly advantageous.

All of the mixing times, diluents, and collection parameters are subject to modification or customization based upon the type of inhaler device, and the active pharmaceutical ingredients and excipients. Background particulate limits are also method specific; therefore, a suitability test is important to determine background particulate limits whereby corrected particle counts can be obtained.

The advantages of the present invention are clear. Particulate matter is sampled as an emitted dose and analyzed directly from the receptacle used to collect the dose, therefore limiting the possibility of introducing additional extraneous particulate matter. The suspended magnetic stir-bar in the collection chamber maintains solution homogeneity without generating additional particulate matter that might otherwise occur if there was scraping/rubbing on the filter used to collect the sample, or by contact of a stirring element with the internal wall of the collection chamber. Laborious manual counting techniques are eliminated in the present invention since particulate matter can be enumerated in the automated fashion by use of a particle counter.

Although the present invention has been disclosed with respect to one or more preferred embodiments, it shall be understood that various other changes and modifications to the present invention can be made commensurate with the scope of the claims appended hereto.

What is claimed is:

1. A particulate matter collection apparatus comprising:
a body defining a collection chamber therein;
a vacuum adapter removably connected to a first end of said body, said vacuum adapter having an orifice communicating with a vacuum source, and said vacuum adapter having a filter seat disposed therein;
a filter placed on said filter seat of said vacuum adapter;
an end cap removably connected to a second end of said body; and a stir-bar assembly mounted in said collection chamber, said stir-bar assembly including a rotatable magnetic stir-bar suspended in said collection chamber.

2. An apparatus, as claimed in claim 1, wherein:
said collection chamber is cylindrical shaped.

3. An apparatus, as claimed in claim 1, wherein:
said filter seat protrudes from a base of said vacuum adapter, said filter seat including an upper surface with a plurality of grooves formed thereon and communicating with said orifice thereby distributing a vacuum across said filter when said vacuum source is activated.

4. An apparatus, as claimed in claim 1, wherein:
said second end of said body has a flange extending beyond said body to receive said end cap.

5. An apparatus, as claimed in claim 1, wherein:
said stir-bar assembly further includes;
at least one support extending transversely across said chamber to mount said stir-bar assembly within said chamber;
a base secured to said support and said rotatable magnetic stir-bar extending from said base;
a pin mounted in said base and connected to said magnetic stir-bar thereby facilitating rotation of said magnetic stir-bar.

6. An apparatus, as claimed in claim 1, wherein:
said magnetic stir-bar includes four stir-bar sections disposed in spaced relation to one another within said collection chamber.

\* \* \* \* \*